US012765985B2

(12) United States Patent
Tredinnick

(10) Patent No.: US 12,765,985 B2
(45) Date of Patent: Oct. 20, 2026

(54) SURGICAL GUIDE

(71) Applicant: Ossability Limited, Christchurch (NZ)

(72) Inventor: Seamus John Tredinnick, Christchurch (NZ)

( * ) Notice: Subject to any disclaimer, the term of this patent is extended or adjusted under 35 U.S.C. 154(b) by 0 days.

(21) Appl. No.: 18/864,611

(22) PCT Filed: May 11, 2023

(86) PCT No.: PCT/NZ2023/050052
§ 371 (c)(1),
(2) Date: Nov. 11, 2024

(87) PCT Pub. No.: WO2023/219519
PCT Pub. Date: Nov. 16, 2023

(65) Prior Publication Data

US 2025/0302598 A1 Oct. 2, 2025

(30) Foreign Application Priority Data

May 12, 2022 (NZ) ........................................ 788157

(51) Int. Cl.
*A61D 1/00* (2006.01)
*A61B 17/15* (2006.01)
*A61B 17/17* (2006.01)

(52) U.S. Cl.
CPC .............. *A61D 1/00* (2013.01); *A61B 17/157* (2013.01); *A61B 17/1764* (2013.01)

(58) Field of Classification Search
CPC ....... A61B 17/15; A61B 17/151; A61B 17/17; A61B 17/1739; A61D 1/00
See application file for complete search history.

(56) References Cited

U.S. PATENT DOCUMENTS

| | | | | |
|---|---|---|---|---|
| 10,682,195 | B2 | 6/2020 | Tredinnick et al. | |
| 2005/0267484 | A1* | 12/2005 | Menzner | A61B 17/15 606/87 |
| 2008/0228189 | A1 | 9/2008 | Fox et al. | |
| 2018/0028272 | A1* | 2/2018 | Tredinnick | A61B 17/1764 |
| 2021/0077122 | A1 | 3/2021 | Reeve et al. | |

FOREIGN PATENT DOCUMENTS

| | | | |
|---|---|---|---|
| EP | 2092899 | A2 | 8/2009 |
| NZ | 734604 | A | 3/2019 |
| WO | WO-2022025775 | A1 | 2/2022 |

OTHER PUBLICATIONS

Mensel, C., 'Preoperative templating in orthopaedic fracture surgery: The past, present and future', Injury, vol. 53, Supplement 3, 2022, pp. S42-S46, <https://doi.org/10.1016/j.injury.2022.09.005\>(https://www.sciencedirect.com/science/article/pii/S002013832200660X).
International Search Report of the ISA issued in PCT/NZ2023/050052, mailed Aug. 4, 2023; ISA/AU.

* cited by examiner

*Primary Examiner* — Si Ming Ku

(57) ABSTRACT

A surgical guide adapted to receive and guide a surgical instrument for performing a bone osteotomy, the surgical guide including a body formed as an elongate block, the block further including first and second fixation apertures, the second fixation aperture adapted to receive a secondary fixation device on a second angle oblique to angle of the first fixation aperture, one or more further positioning apertures and a cutting channel.

11 Claims, 9 Drawing Sheets

SURGICAL GUIDE

CROSS-REFERENCE TO RELATED APPLICATIONS

This application is a 371 U.S. National Phase of International Application No. PCT/NZ2023/050052, filed on May 11, 2023, which also claims priority to New Zealand Patent Application 788157 filed on May 12, 2020. The entire disclosure of the above applications are incorporated herein by reference.

FIELD OF INVENTION

This invention relates to a surgical guide. More specifically, the invention relates to a surgical osteotomy guide that may be used in canine tibial tuberosity advancement and other orthopaedic or surgical procedures.

BACKGROUND TO THE INVENTION

Tibial tuberosity advancement (TTA) procedures are performed to repair deficient cranial cruciate ligaments in dogs. Currently used TTA procedures include the TTA Rapid™ procedure developed by Rita Leibinger Medical. This procedure allows an osteotomy to be made through a section of the proximal tibia allowing the tibial tuberosity to be advanced outwardly, the advanced tuberosity then held in position using a corresponding tibial tuberosity implant, typically in the form of a wedge. Such advancement of the tibial tuberosity stabilises the stifle joint by changing the angle of the patella ligament and reducing tibiofemoral shear forces during weight bearing.

The TTA Rapid procedure includes the use of a saw and drill guide to assist the surgeon in correctly positioning the tibial osteotomy. In this procedure, a pin is located at the at the top of the osteotomy at the proximate end of the tibia, then an L-shaped guide placed over the pin at a specific point to determine the required osteotomy length. A second peg is placed in the foot of the L-shaped guide to determine the osteotomy angle, then the peg pushed and held against the tibia while the osteotomy is being performed. However, the angle of the osteotomy is dependent on the guide being successfully held/pushed against the tibia while the osteotomy is underway, opening up a risk of movement of the guide during the osteotomy, or an incorrect osteotomy angle.

Typically, the osteotomy is an oblique angle from the longitudinal axis of the tibia and when using known saw guides, this angle is estimated each time the saw guide is positioned. By having to estimate the angle at which to place the drill guide, it is not possible to reproduce a successful surgery on further patients, and leaves the surgeon open to errors in judgement when placing the guide.

An osteotomy performed at an incorrect angle may result in patellar luxation, corresponding implants not having an optimal fit within the space provided or may affect the degree to which the tuberosity is able to be advanced, as well as potentially jeopardising the long-term success of the TTA operation.

Other known osteotomy guides include the TTA guide outlined in NZ734604, which includes a central guide with moveable lugs that can be positioned to correctly determine a correct osteotomy position. Guides such as these are expensive to produce and are therefore suited to be used multiple times with sterilization required in between each use, which takes both time and money. In order for the instrumentation to always be readily available for use, a number of such guides may be needed, adding to the expense.

Guides with moving parts can also add complexity to a surgical plan. Correct alignment is required for each patient and the accurate planning and movement of the guides is needed each time to ensure the guide is accurately used in each patient.

It would be advantageous to produce a low cost, single use guide that may be readily usable across a range of patients and anatomies, that addresses some of these disadvantages.

OBJECT OF THE INVENTION

It is an object of the invention to provide a surgical guide that provides a set of parameters for guiding tibial osteotomies in tibial tuberosity advancement procedures and other orthopedic procedures.

Alternatively, it is an object of the invention to at least provide the public with a useful choice.

SUMMARY OF THE INVENTION

According to one aspect of the invention there is provided a surgical guide adapted to receive and guide a surgical instrument for performing a bone osteotomy, the surgical guide including a body formed as an elongate block, the block further including;

- a first fixation aperture extending through a portion of the block, the first fixation aperture adapted to receive a primary fixation device on a first angle;
- a second fixation aperture extending through a portion of the block, the second fixation aperture adapted to receive a secondary fixation device on a second angle oblique to the first angle; and
- one or more further positioning apertures extending through a portion of the block, the one or more positioning apertures adapted to receive one or more positioning devices; and
- a cutting channel.

According to a further aspect of the invention, there is provided a surgical guide for receiving and guiding a surgical instrument performing a bone osteotomy, the guide including a body shaped as an elongate irregular polyhedral block, the block including;

- at least one cutting channel extending through the block, the cutting channel having a discrete length such that the channel is bounded by the block through which it extends;
- two or more fixation apertures extending through the block, each fixation aperture adapted to receive a fixation device; and
- one or more positioning apertures extending through the block, the positioning aperture(s) adapted to receive a positioning device.

In preferred embodiments the block includes a single plane of symmetry.

In preferred embodiments the block is formed as an elongate irregular polyhedron with 6-20 polygonal faces, more preferably 12-14 faces.

Preferably, the block is tapered in at least one direction.

Preferably, apertures in the block are cylindrical in shape. More preferably, the apertures are formed as straight, angled or tapered cylinders.

In further preferred embodiments, the block includes a cutting channel extending through the block, the cutting channel fluidly connected to a fixation aperture at a first end. More preferably, the cutting channel is fluidly connected to one or more overlapping apertures at a second, opposing end of the channel.

Preferably, the cutting channel is straight, and the overlapping apertures form a single aperture extending from the second end of the cutting channel.

Preferably, the block includes a second line of overlapping positioning apertures parallel to the cutting channel.

Preferably, the block includes a third line of overlapping positioning apertures parallel to the second line of overlapping apertures.

Preferably, each line of overlapping apertures includes 12-30 overlapping cylindrical shaped positioning apertures extending through the block.

Preferably, the block is formed from a polymer-based material and the apertures are sized and/or shaped to retain a surgical pin.

In preferred embodiment the block includes at least two fixation apertures, at least two of the fixation apertures obliquely angled from each other and extending through the block.

More preferably, the block includes a first fixation aperture at a first end of the cutting channel and a second fixation aperture proximate to and obliquely angled from the first fixation aperture. Even more preferably, the block includes a third fixation aperture proximate to and angled from the first fixation aperture.

In alternative embodiments, the fixation apertures and/or positioning apertures are discrete apertures, or a combination of discrete and overlapping apertures.

Preferably the guide includes one or more measurement and/or alignment markings on the block surface.

Preferably, the measurement and/or alignment markings are directed to the use of the guide on a patient's left side on a first side and directed to the use of the guide on a patient's right side on an opposing side.

Preferably, in use, the surgical guide is suitable for use in a left side configuration in a first orientation, and suitable for use in a right side configuration following a 180 degree turn along the cutting channel longitudinal axis.

According to a further aspect of the invention there is provided a method for surgical planning of an orthopedic osteotomy procedure, the method including;

a) performing an x-ray on the relevant patient bone;
b) overlaying the surgical guide as described above on the x-ray to determine optimal osteotomy position;
c) establishing a first pin placement position of a primary fixation pin in the first fixation aperture;
d) orienting the guide to select the required osteotomy position;
e) determining placement of the two positioning pins based on optimal bone abutment; and
f) selecting the desired osteotomy length based on the patient x-ray.

According to further embodiments there is provided a method for guiding an osteotomy tool using the surgical guide described above, the method including the steps of;

a) determining one or more preferred osteotomy positions on a patient body;
b) aligning the guide as described above with an anatomical location on a patient using one or more positioning devices;
c) fixing the guide in position on a patient using a fixing device located within one or more apertures on the surgical guide;
d) guiding the osteotomy tool through or partially through the at least one cutting channel in the surgical guide.

According to further embodiments there is provided a surgical guide kit, the kit including;

a surgical guide as described above;
two or more fixation devices; and
one or more positioning devices.

Further aspects of the invention, which should be considered in all its novel aspects, will become apparent to those skilled in the art upon reading of the following description which provides at least one example of a practical application of the invention.

BRIEF DESCRIPTION OF THE DRAWINGS

One or more embodiments of the invention will be described below by way of example only, and without intending to be limiting, with reference to the following drawings, in which.

DETAILED DESCRIPTION OF PREFERRED EMBODIMENTS OF THE INVENTION

The surgical guide of the present invention is designed for use as an off-the-shelf component that can be made as a single-use guide, or as a multi-use guide.

Single-use guides are preferably made from polymer materials, for example nylon, or the guide may also be made with metals suitable for surgical guides such as stainless steel. The guide may be injection molded, made using additive manufacturing such as selective laser sintering (SLS) or machined depending on the materials used.

For explanatory purposes the description below will refer the use of the guide when performing a TTA procedure, however this is not intended to be limiting in any way. The surgical guide may be used as a guide for a range of surgical procedures in both animals and humans where a guide is required for drill or pin placement, performing an osteotomy or for guiding any other suitable instrumentation.

Surgical guides are used to improve the accuracy and repeatability of technically demanding surgery. Tibial tuberosity advancement (TTA) is a technically demanding corrective ('cut and move') procedure to reposition anatomy and change the direction of forces around a stifle to compensate for a damaged or ruptured cruciate ligament.

The placement of the osteotomy is determined by the size and geometry of bone stock in both the tuberosity and tibia, affecting the bone's ability to resist weight bearing and locomotive force during convalescence.

An 'optimal' osteotomy can be determined by the relative size and geometry of the tuberosity and tibia to minimise the risk of fracture.

Using the surgical guide of the present invention, the osteotomy can be planned using a 2D radiograph (X-ray) prior to surgery. The surgical guide can then be configured to accurately reproduce the location of the planned osteotomy on the real patient anatomy. This enables the user to translate an intended optimal surgical plan to the physical patient to minimise the risk of complication.

The surgical guide of the present invention will be described further in non-limiting terms below with reference to FIGS. 1-10.

Figure 1:
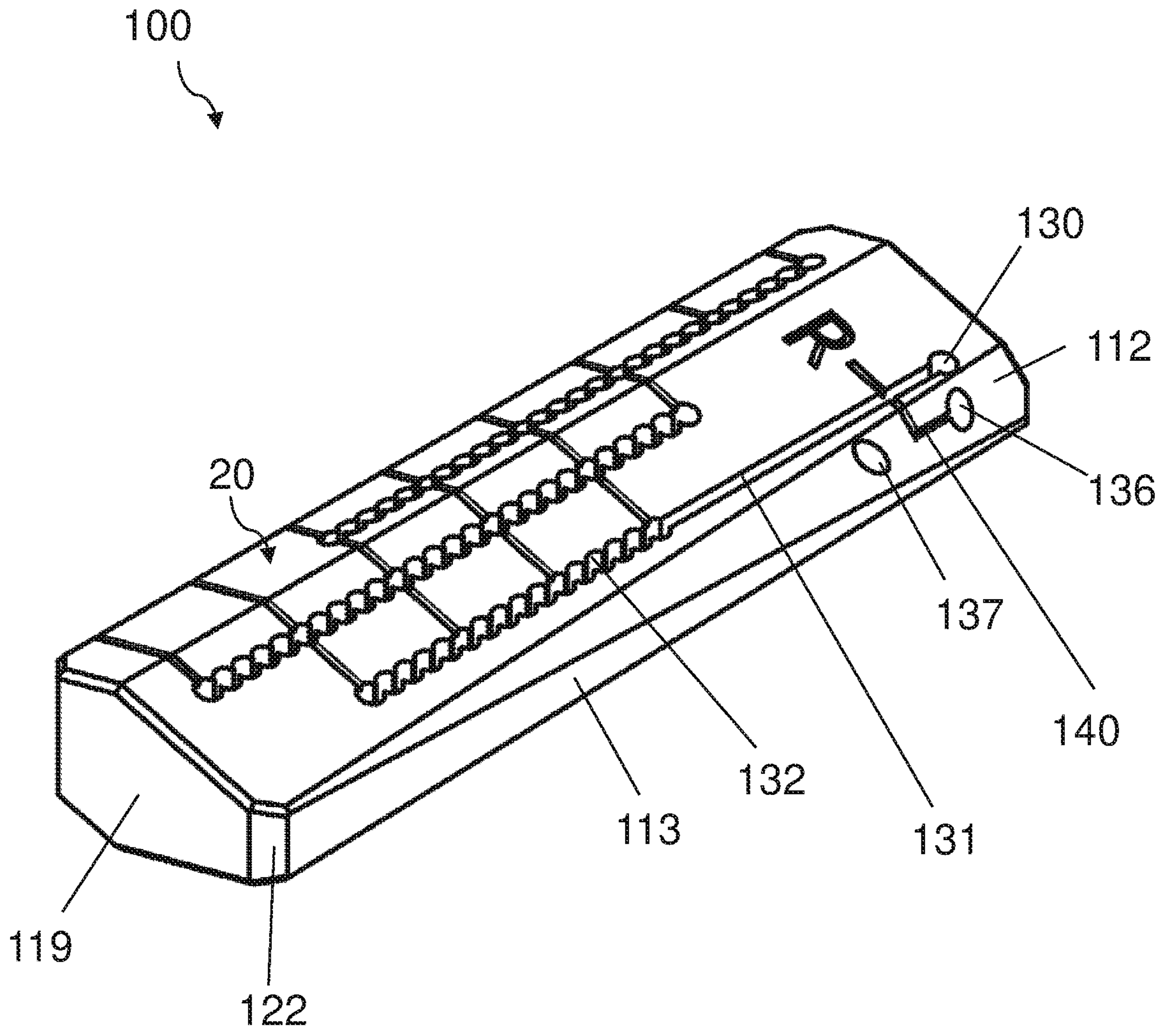
FIG. 1 shows a top perspective view of a surgical guide in one embodiment of the invention showing the markings for a right-side procedure.
Figure 2:
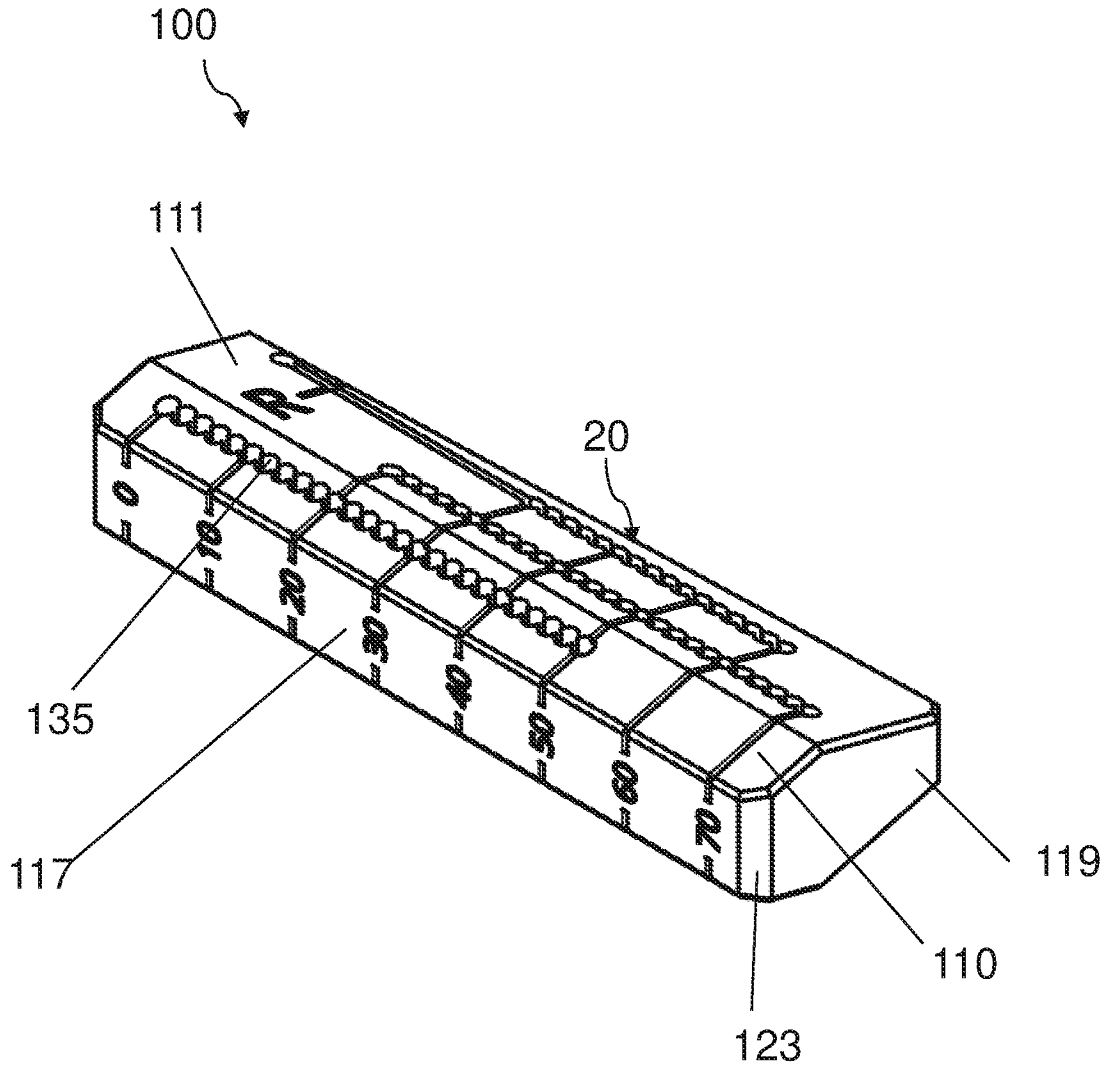
FIG. 2 shows a further top perspective view of the surgical guide of FIG. 1.
Figure 3:
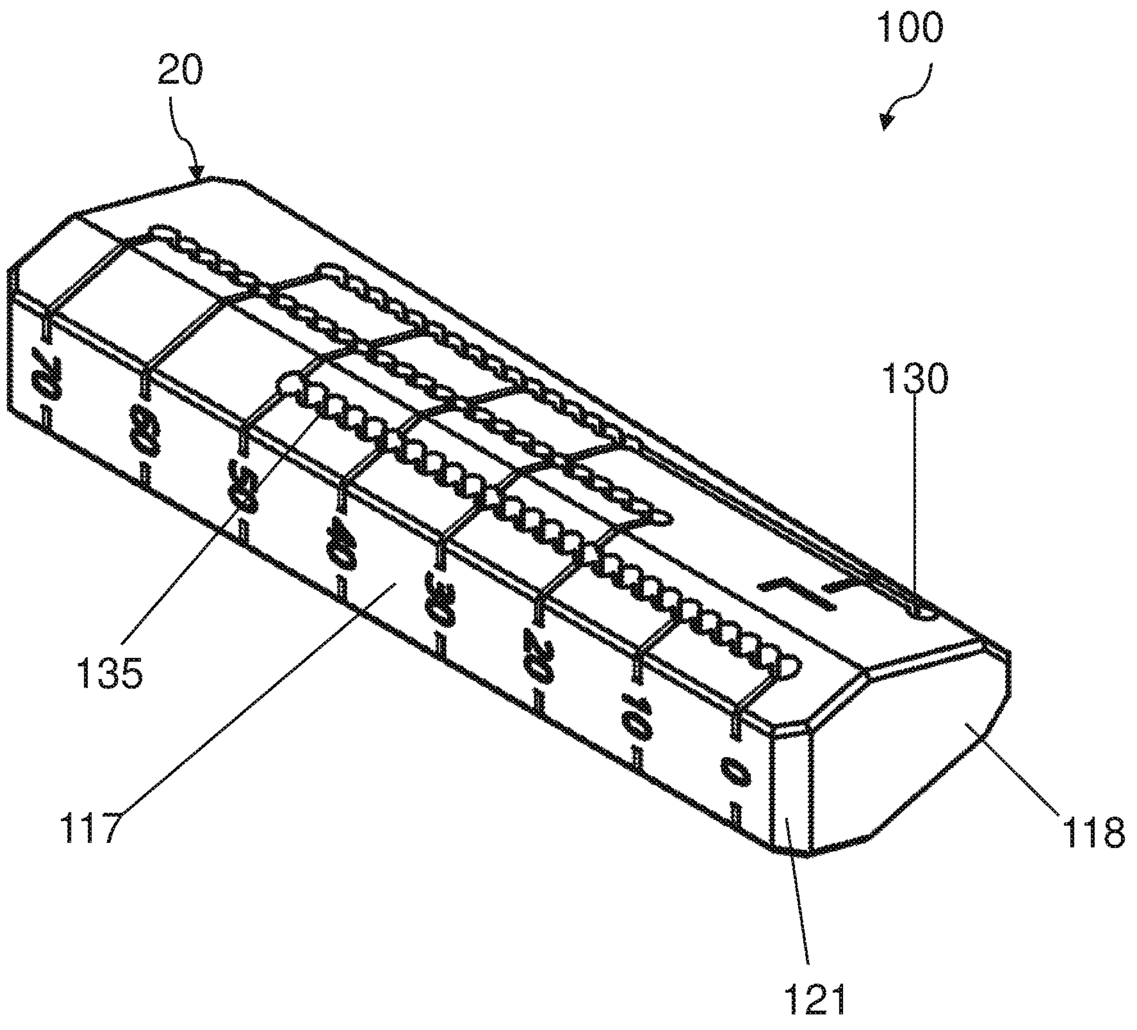
FIG. 3 shows an bottom perspective view of the surgical guide of FIG. 1 showing the markings for a left-side procedure.

FIGS. 1-4 show perspective views of a surgical guide 100 in one example of the invention. FIGS. 1 and 2 show guide 100 from a top perspective view with markings and guide apertures adapted for use with a procedure performed on the right leg, or right-hand side of a patient. The surgical guide 100 has a single horizontal plane of symmetry A (see FIG. 8), such that a 180-degree rotation of the guide along the elongate axis of the block allows the user to view and utilize the markings and guide apertures adapted for the left leg or left-hand side of a patient. This symmetry provides a simple, convenient guide that is ready for use with any TTA procedure, without the need for specially oriented guides for each limb.

Guide 100 is preferably formed as a single-piece block 20 with no moving parts. Block 20 is preferably formed as an irregular polyhedron, with preferably from 6-20 polygonal faces making a multi-contoured block. In the design shown, block 20 is formed with 14 polygonal faces 110-123 of varying shapes, creating a contoured block having a wider region defined by faces 110, 116, 117, 121 and 123 tapering to a narrow region defined by faces 111-115, 120 and 122. The polygonal faces may be irregular polygons, or may be triangular, square, rectangular, rhomboid, hexagonal, octagonal, or heptagonal for example. Edges or vertices between the faces may be beveled, curved or straight.

Figure 8:
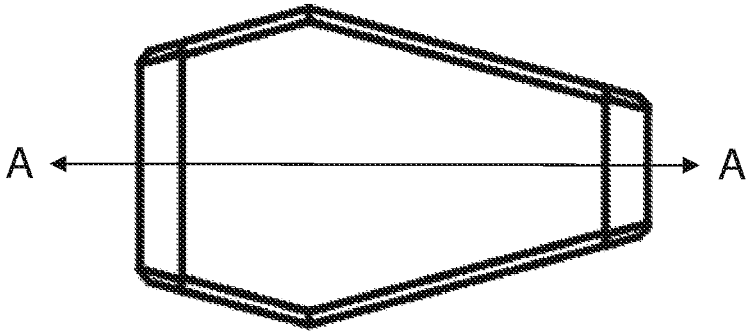
FIG. 8 shows a top end view of the guide of FIGS. 1-4.

The guide may include a horizontal plane of symmetry as shown by "A-A" in FIG. 8 to enable a single guide to be used for both left and right-side procedure, or the guide may be designed without a plane of symmetry such that separate guides are used for left and right-handed procedures. In embodiments where symmetry isn't required, a bone-face surface of the block 20 may include contours that conform to the shape of bone the guide is rested on during a surgical procedure. The guide may also be formed as a block with predominantly curved surfaces (not shown), rather than angular polygonal surfaces, or may be formed with a combination of both.

Guide 100 includes a primary fixation aperture 130 extending through block 20 from face 111 to face 115 and is shaped for receiving a primary fixation device such as a surgical pin. The primary fixation aperture 130 is substantially cylindrical and is oriented to be substantially vertical when guide 100 is in position on a patient, and is positioned at the end of block 20 proximal face 118. Aperture 130 provides a means to insert a primary fixation device that will both secure the guide in position, and act as a stopping means in a TTA procedure to ensure the patella tendon is protected during an osteotomy.

Cutting channel 131 extends from aperture 130 partially along the elongate length of block 20 and preferably runs parallel to the adjoining edges of faces 110 and 111 on the right side and adjoining edges of faces 115 and 116 of the left side of block 20. Cutting channel 131 extends completely through block 20 from face 111 to face 115, providing a guide for an osteotomy saw to enter and saw through the bone beneath guide 100. Cutting channel 131 is preferably straight in the current embodiment but may be curved or partially curved in other embodiments not shown.

Channel 131 is sized to fit a range of commonly used orthopedic saw blades. The channel 131 is preferably bounded by straight and/or smooth walls along at least a portion of the channel length to guide a saw blade as smoothly as possible. As seen in the figures, opposing walls of one end of cutting channel 131 distal from primary fixation aperture 130 are curved or scalloped in shape symmetrically to each other to to discretely receive and align one or more one or more fixation devices, preferably cylindrical fixation devices such as a pin. For the purposes of this specification this arrangement is also described as a row of overlapping apertures 132. It should be understood that a row of overlapping cylindrical apertures forms a continuous, fluidly connected channel, but each section of the channel that is formed with and defined by opposing curved edges will be referred to as one overlapping aperture for ease of description.

The scalloped walls preferably include overlapping apertures 132 of a number to receive and hold, or help position a fixation device every 2 mm, and as shown in the figures preferably sixteen overlapping apertures 132 on each wall, able to locate pins in sixteen discrete locations along the cutting channel 131. The terminal end of cutting channel 131 is formed with a final overlapping aperture adapted to receive the pin or other fixation device.

In other examples not shown, the cylindrical apertures are not overlapping and may be spaced apart along cutting channel 131, such that instead of channel 131 being formed from a number of overlapping cylindrical apertures as shown in the figures, the channel may include a line of discrete cylindrical apertures fluidly connected by straight walled channel running centrally through the line of cylindrical apertures.

Overlapping apertures 132 may be used to receive a fixation device such as a surgical pin and may be used for either securing the guide to the bone or locating the guide in the correct position on the patient. A pin received within any one of overlapping apertures 132 may also be used to indicate the end point of a desired osteotomy if required. Preferably, block 20 includes between 2-30 overlapping apertures 132, more preferably, 12-20. Sixteen overlapping apertures 132 are shown in the preferred embodiment shown in the Figures. In practice, the overlapping apertures may be of any number such that a cutting channel of a required length may be achieved.

Block 20 includes two further lines of overlapping, preferably cylindrical apertures 134 and 135 that extend through block 20. Overlapping apertures 134 extend through block 20 from face 111 to face 115, while overlapping apertures 135 are substantially parallel to apertures 134 and extend through block 20 from face 110 to face 116. Overlapping apertures 134 and 135 are preferably parallel to cutting channel 131 and are adapted to receive a pin, peg, lug or wire to act or other positioning device that is extendable through apertures 134 and/or 135 to create a means to abut against a patient bone during surgery.

In other embodiments not shown, line(s) of overlapping apertures, or non-overlapping apertures may be placed in other locations relative to the cutting channel, or at a range of angles through block 20 compared to the vertical axis of the cutting channel, from 1°-90°.

The position of the overlapping apertures for positioning may also change if position needs to be controlled from different directions, for example for pre-operative planning where a range of different X-rays may be taken on different planes.

Two lines of overlapping apertures as shown in the drawings is preferable when the guide is to be used in a TTA procedure, and the range of different aperture positions available maximise the combinations of pin placements available. This is particularly useful in larger canines.

When guide 100 is formed using a polymer-based material, apertures 130, 132, 134 and 135 are shaped/sized to ensure an interference fit between the pin and walls of the aperture, helping to retain the pin within the aperture(s). When guide 100 is formed using metal, pins may be retained within the apertures using another method, such as a clamp, spring, tape, or a silicone ring for example.

To fix guide 100 in position for the osteotomy, one or more fixation apertures (in this embodiment, two apertures) 136, 137 are formed proximal to and obliquely in relation to substantially vertical aperture 130.

Figure 4:
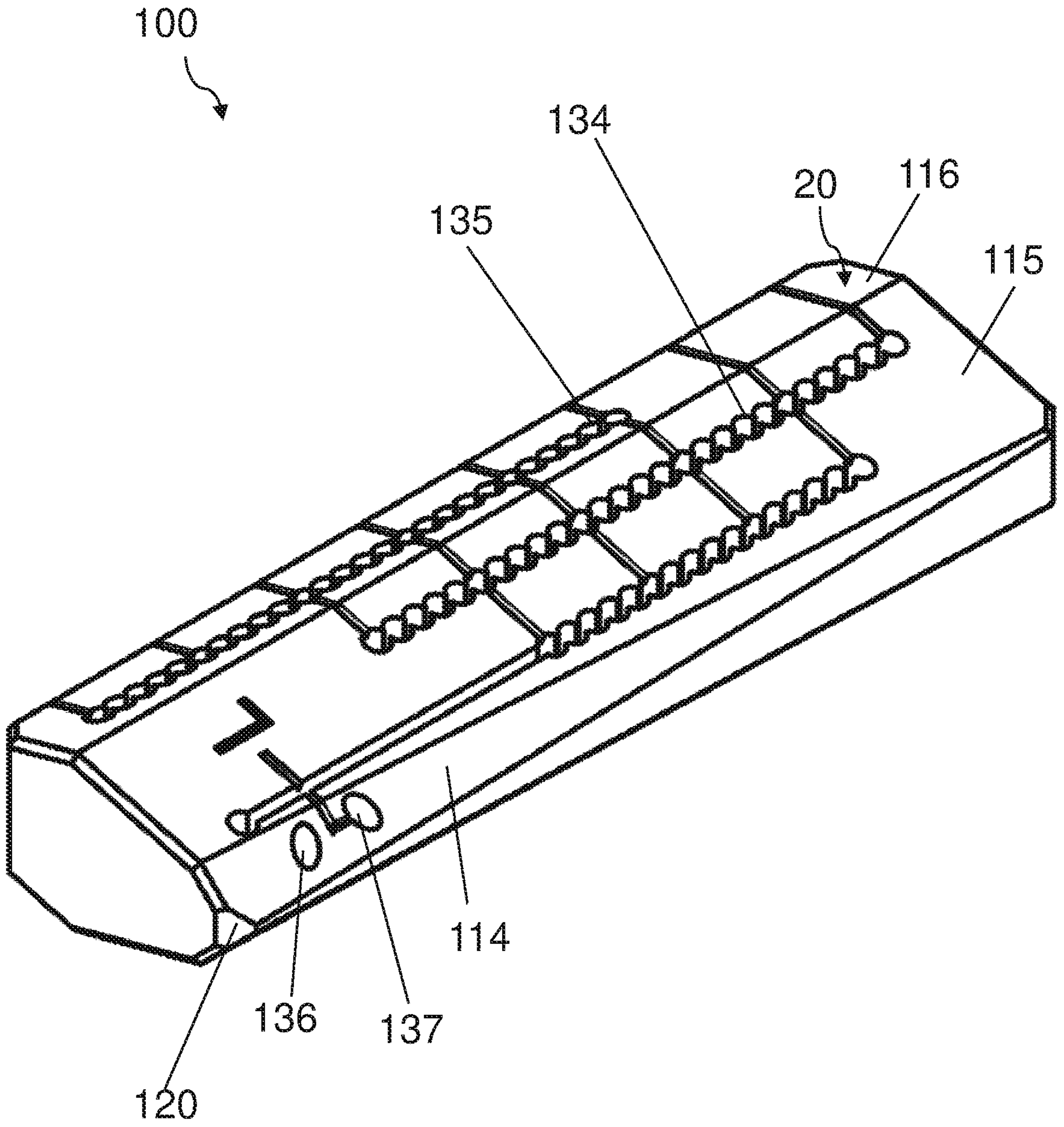
FIG. 4 shows a further bottom perspective view of the surgical guide of FIG. 3.
Figure 9:
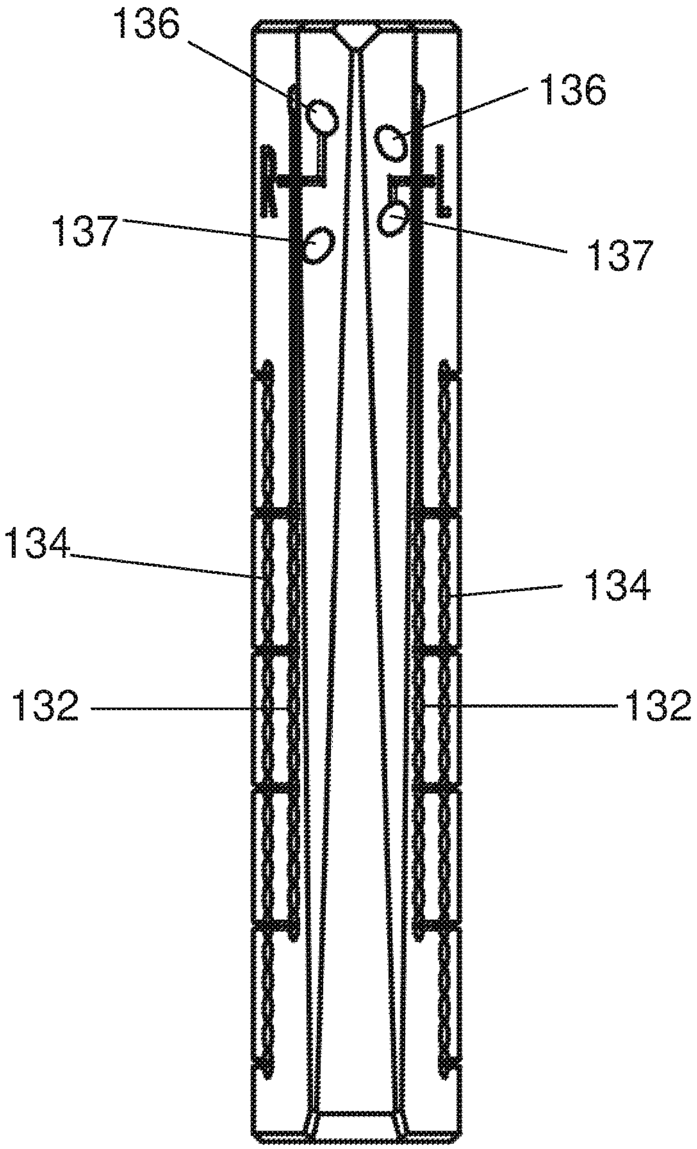
FIG. 9 shows a right side view of the guide of FIGS. 1-4.

Fixation apertures 136, 137 are adapted to receive a fixation device such as a surgical pin on an angle to secure the guide to the patient, with fixation aperture 136 designed for use with a right-hand procedure and fixation aperture 137 designed for use with a left-hand procedure. In use, one of either fixation aperture 136 or 137 is used during the procedure and as can be seen in FIGS. 1, 4 and 9, an indication line or marking 140 is incorporated into the block 20 to identify the correct fixation aperture to be use for securing the guide, depending on which side of the block is facing up. The selection of the correct fixation aperture to insert an oblique pin ensures the pin aims away from the tibial plateau, thereby avoiding damage to the articular surfaces.

The inclusion of one or more obliquely positioned pin means the guide cannot side away from the bone along the other parallel pins.

Measurement and alignment markings may be incorporated into block 20 to aid in preparing a positioning plan and for placing the guide on the patient during surgery. Markings may be in the form or lines, dots, dashes, numbers, or notches for example and may be integrally formed on the surface on block 20 or applied post-manufacture.

Figure 5:
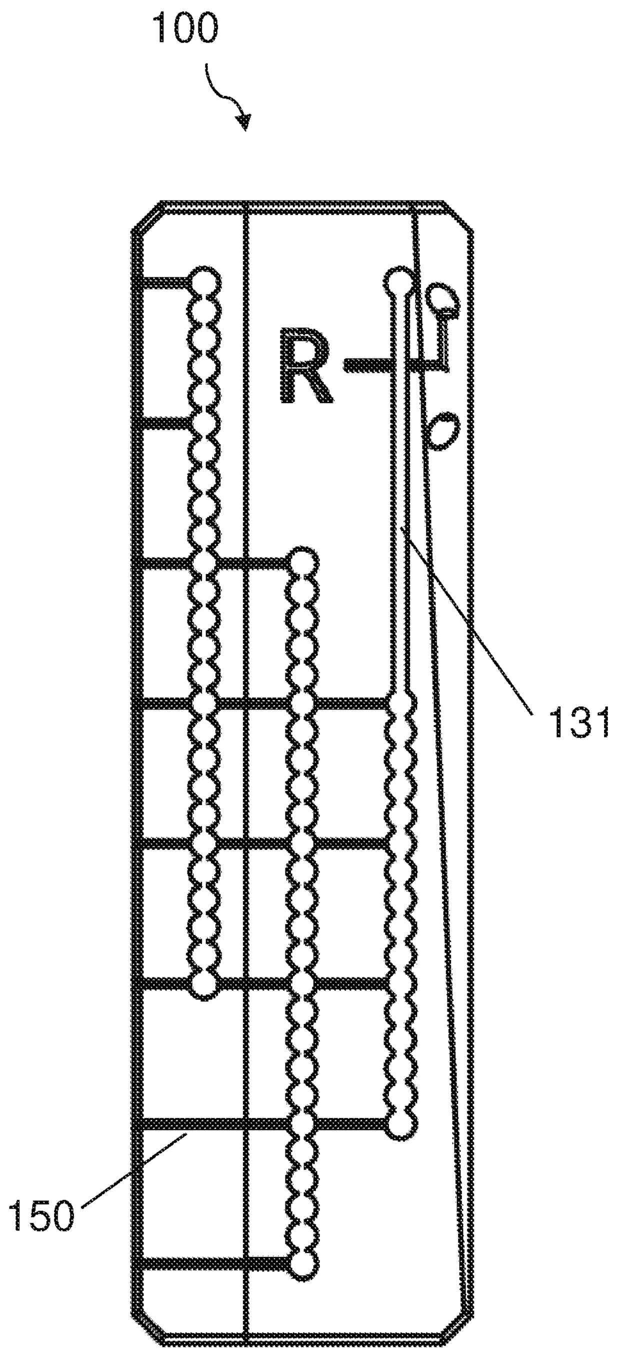
FIG. 5 shows a top view of the surgical guide of FIGS. 1-4.
Figure 6:
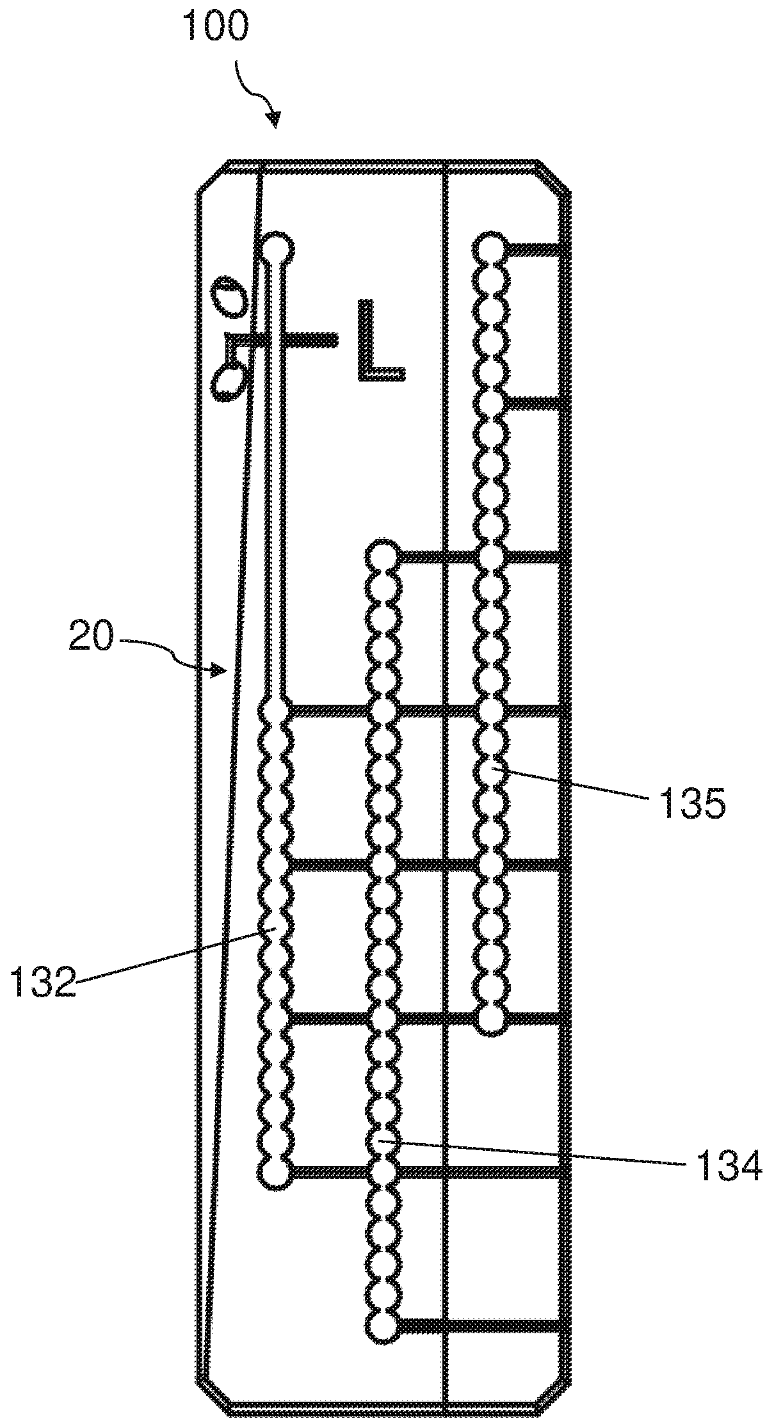
FIG. 6 shows a bottom view of the surgical guide of FIGS. 1-4.
Figure 7:
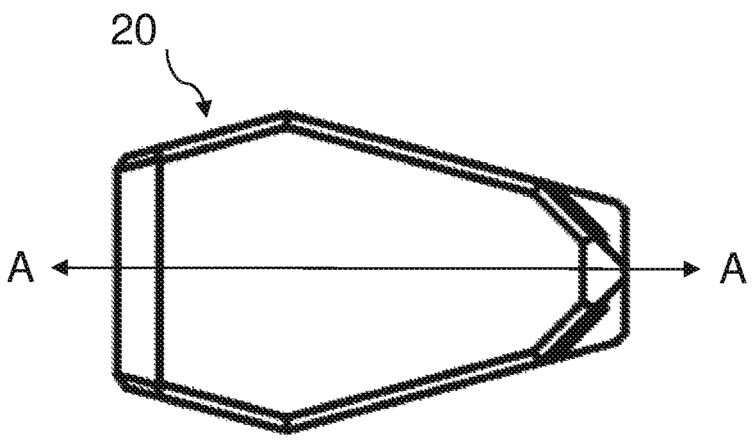
FIG. 7 shows a bottom end view of the guide of FIGS. 1-4.
Figure 10:
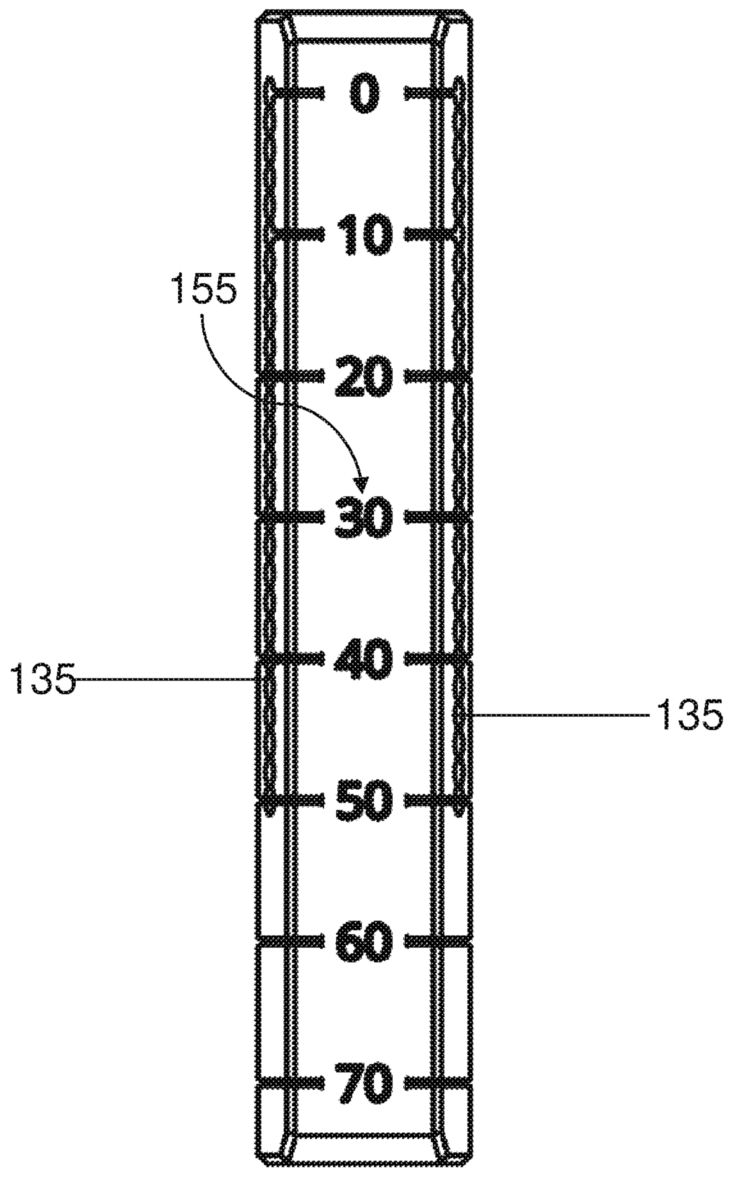
FIG. 10 shows a left side view of the guide of FIGS. 1-4.

As seen in FIGS. 5 and 6, block 20 includes a series of parallel lines 150 perpendicular to the overlapping rows of apertures 134, 135 and cutting channel 131, to visually aid identification of the correct aperture for pin placement. FIGS. 4 and 10 show the inclusion of a measurement ruler 155 incorporated into face 117 of block 20. This measurement ruler further helps with pin placement and the accurate transfer of information surrounding pin placement and osteotomy length from the pre-operative plan to the surgery itself.

In use, guide 100 of the present invention can be used both during a surgical osteotomy procedure and for pre-operative planning prior to surgery. In pre-operative planning for a canine TTA procedure, an X-ray image is taken of the tibia. Guide 100 is then placed over the X-ray and aperture 130 aligned on a desired starting location, often a specific anatomical landmark such as the Gerdy's tubercle. The guide is then rotated using aperture 130 as a fulcrum, until cutting channel 131 is aligned with the desired osteotomy position.

With reference to the X-ray, a desired positioning pin placement is determined that would enable positioning devices inserted into one or more of the overlapping apertures 134 and 135 to abut the anterior edge of the tibia when guide 100 is positioned on the proximal craniomedial face of the tibia. These pin positions create a two-dimensional "profile" that matches the anatomical contours of the bone to uniquely locate the surgical guide.

Once the desired pin placement has been determined, the guide is ready for use in surgery. During the TTA procedure, positioning pins are inserted into the predetermined positions in overlapping apertures 134 and 135. A primary fixation pin is inserted into aperture 130 and enters the bone in the predetermined location. Guide 100 is then rotated around the pin in aperture 130 until positioning pins inserted into apertures 134 and 135 abut the anterior edge of the tibia, indicating a positive placement of guide 100.

A fixation pin is then inserted through either fixation aperture 136 or 137, depending on whether the felt or right side of the guide is being used, and into the bone as required, securing guide 100 in position.

If further securing of the guide is required, additional fixation pins may be inserted into any one of the overlapping apertures 132, 134 or 135. Preferably, the optimal fixation positions are determined pre-operatively based on bone strength and thickness.

The osteotomy is then completed, with the desired osteotomy length marked using a pin in one of positioning apertures 132. Fixation pins are then extracted and guide 100 removed. The additional steps of the TTA procedure can then commence.

The entire disclosures of all applications, patents and publications cited above and below, if any, are herein incorporated by reference.

Reference to any prior art in this specification is not, and should not be taken as, an acknowledgement or any form of suggestion that that prior art forms part of the common general knowledge in the field of endeavour in any country in the world.

Where in the foregoing description reference has been made to integers or components having known equivalents thereof, those integers are herein incorporated as if individually set forth.

It should be noted that various changes and modifications to the presently preferred embodiments described herein will be apparent to those skilled in the art. Such changes and modifications may be made without departing from the spirit and scope of the invention and without diminishing its attendant advantages. It is therefore intended that such changes and modifications be included within the present invention.

The invention claimed is:

1. A surgical guide adapted to receive and guide a surgical instrument for performing a bone osteotomy in a canine tibial tuberosity advancement (TTA) procedure, the surgical guide comprising:

a body formed as an irregular polyhedral block, the irregular polyhedral block further comprising:

an elongate cutting channel extending in a straight line longitudinally along at least a portion of a length of the user-facing surface between a first end and a second end and extending through the irregular polyhedral block from the user-facing surface to the opposing bone-facing surface, the elongate cutting channel having a discrete length such that the elongate cutting channel is bounded by the irregular polyhedral block through which it extends;

a first fixation aperture extending through a portion of the irregular polyhedral block from a user-facing surface to an opposing bone-facing surface, the first fixation aperture configured to receive a primary fixation device on a first angle;

a second fixation aperture extending through a portion of the irregular polyhedral block from the user-facing surface to the opposing bone-facing surface, the second fixation aperture configured to receive a secondary fixation device on a second angle oblique to the first angle, wherein the second fixation aperture is located on a first lateral side of the cutting channel;

at least two positioning apertures extending through a portion of the irregular polyhedral block from the user-facing surface to the opposing bone-facing surface, the at least two positioning apertures configured to receive one or more positioning devices configured to, when received, abut an anterior edge of a tibial bone surface;

wherein the at least two positioning apertures comprise a first positioning aperture and a second positioning aperture, each located on an opposing lateral side of the elongate cutting channel from the second fixation aperture and spaced apart from the longitudinal axis of the cutting channel;

wherein the first positioning aperture is located substantially perpendicular to a mid-portion of the elongate cutting channel positioned between the first end and the second end, and the second positioning aperture is located substantially perpendicular to the second end of the elongate cutting channel;

wherein a substantially perpendicular distance of the first positioning aperture from the longitudinal axis of the elongate cutting channel is greater than a second substantially perpendicular distance of the second positioning aperture from the elongate cutting channel.

2. The surgical guide of claim 1, wherein the second fixation aperture is adjacent to the first fixation aperture.

3. The surgical guide of claim 1, wherein the irregular polyhedral block is formed as an elongate irregular polyhedron with 6-20 polygonal faces.

4. The surgical guide of claim 1, wherein the irregular polyhedral block is tapered in at least one direction.

5. The surgical guide of claim 1, wherein the first fixation aperture is located at a first end of the elongate cutting channel and the elongate cutting channel extends from the first fixation aperture located at the first end of the elongate cutting channel to an opposing second end of the elongate cutting channel.

6. The surgical guide of claim 1, wherein one or more of the first fixation aperture, second fixation aperture or at least one positioning apertures are cylindrical in shape.

7. The surgical guide of claim 6, wherein one or more of the first fixation aperture, second fixation aperture or at least one positioning apertures are formed as straight, angled, or tapered cylinders.

8. The surgical guide of claim 1, wherein the irregular polyhedral block is formed from a polymer-based material and the first fixation aperture, second fixation aperture or at least one positioning apertures are sized and/or shaped to retain a surgical pin.

9. The surgical guide of claim 1, wherein the guide includes one or more measurement and/or alignment markings on the irregular polyhedral block surface.

10. The surgical guide of claim 1, wherein the bone-facing surface comprises contours that conform to a shape of the facing bone surface.

11. A surgical guide kit, the surgical guide kit including;

a surgical guide as claimed in claim 1;

at least two fixation devices; and at least two positioning devices.

* * * * *